(12) United States Patent
Kim (10) Patent No.: US 8,263,333 B2
(45) Date of Patent: Sep. 11, 2012

(54) METHOD OF ANALYZING A TARGET NUCLEIC ACID SEQUENCE

(75) Inventor: Byung-chul Kim, Suwon-si (KR)

(73) Assignee: Samsung Electronics Co., Ltd., Samsung-ro, Yeonftong-gu, Suwon-si, Geyonggi-do (KR)

( * ) Notice: Subject to any disclaimer, the term of this patent is extended or adjusted under 35 U.S.C. 154(b) by 259 days.

(21) Appl. No.: 12/644,295

(22) Filed: Dec. 22, 2009

(65) Prior Publication Data

US 2010/0197520 A1    Aug. 5, 2010

(30) Foreign Application Priority Data

Feb. 4, 2009   (KR) .................. 10-2009-0009041

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .................. None
See application file for complete search history.

(56) References Cited

U.S. PATENT DOCUMENTS

| 5,795,714 A | 8/1998 | Cantor et al. |
| 5,942,609 A | 8/1999 | Hunkapiller et al. |
| 6,114,121 A | 9/2000 | Fujiwara et al. |
| 6,403,319 B1 | 6/2002 | Lizardi et al. |
| 6,506,594 B1 | 1/2003 | Barany et al. |
| 2002/0102586 A1 | 8/2002 | Ju et al. |
| 2006/0240443 A1 | 10/2006 | Lodes et al. |

OTHER PUBLICATIONS

Ronaghi, M. et al., Biotechniques, vol. 25, pp. 876, 878, 880-882, 884 (1998).*
Broude, N. E. et al., Nucl. acids res., vol. 29, e92, pp. 1-11 (2001).*
Eggerding, F. A., PCR Meth. Appl., vol. 4, pp. 337-345 (1995).*
Mirzabekov, Trends Biotechnol., vol. 12, pp. 27-32 (1994).*

* cited by examiner

*Primary Examiner* — Teresa E Strzelecka
(74) *Attorney, Agent, or Firm* — Leydig, Voit & Mayer, Ltd.

(57) ABSTRACT

Provided is a method of analyzing a target nucleic acid sequence by using an elongation reaction and a ligation reaction.

29 Claims, 4 Drawing Sheets

METHOD OF ANALYZING A TARGET NUCLEIC ACID SEQUENCE

CROSS-REFERENCE TO RELATED APPLICATIONS

This application claims priority to Korean Patent Application No. 10-2009-0009041, filed on Feb. 4, 2009, and all the benefits accruing therefrom under 35 U.S.C. §119, the contents of which is incorporated herein in its entirety by reference.

BACKGROUND

1. Field

One or more embodiments of the present invention relate to a method of analyzing a target nucleic acid sequence.

2. Description of the Related Art

Methods of analyzing a target nucleic acid sequence are known in the art. For example, methods of analyzing a target nucleic acid sequence include a method of directly analyzing a target nucleic acid sequence. However, methods of directly analyzing a target nucleic acid sequence are often inappropriate when a large number of different target nucleic acids need to be analyzed.

Other methods of analyzing a target nucleic acid sequence include a Restriction Fragment Length Polymorphism ("RFLP") method, an allele-specific polymerase chain reaction ("PCR") method, a Southern blot method or a Northern blot method. However, these methods are expensive and time consuming. In addition, these methods are also inappropriate when a large number of different target nucleic acids need to be analyzed at once.

Additional methods of analyzing a target nucleic acid sequence include a method using a microarray. According to this method, a plurality of probe nucleic acids having known sequences are immobilized on distinct regions of a substrate, and then, the immobilized probe nucleic acids are hybridized with a target nucleic acid. Detection of a target nucleic acid using a microarray is achieved when a target nucleic acid complementary to an immobilized probe nucleic acid hybridizes with the probe and is thus retained on the microarray surface. For example, an aqueous solution containing fluorescent-labeled nucleic acids can be applied to the surface of a microarray to let the nucleic acids hybridize to complementary probes on the microarray surface. The solution is then removed and only target nucleic acids hybridized to the probes on the microarray surface are retained after the procedure. By detecting fluorescence of the fluorescent material labeling the nucleic acids hybridized to probes on the DNA microarray it can be determined whether any target nucleic acids complementary to the probes were present in the sample nucleic acids. Further, the sequence of a nucleic acid can be determined using a microarray, wherein the hybridization results of nucleic acid to the respective probe nucleic acids having known sequences in the distinct regions are measured and then, a target nucleic acid sequence is determined based on the measurement results. For example, the degree of hybridization of a target nucleic acid to two different probe nucleic acids which are identical to each other except for a single nucleotide sequence are compared, and based on the comparison results, it is determined whether the target nucleic acid sequence includes a sequence complementary to either of the two probe nucleic acids. However, since this method is performed based on a difference in signals that vary according to hybridization, specificity and accuracy of the sequence analysis may be low.

Accordingly, even with conventional techniques, there is still a need to develop a method of more effectively analyzing a target nucleic acid sequence.

SUMMARY

Disclosed herein is a method of analyzing a target nucleic acid sequence.

Additional aspects will be set forth in part in the description which follows and, in part, will be apparent from the description, or may be learned by practice of the presented embodiments.

According to one or more embodiments, a method of analyzing a target nucleic acid sequence includes: providing a microarray including a substrate on which a plurality of probe nucleic acids are immobilized; providing a target nucleic acid containing a sequence capable of forming a stem and loop structure in an end of the target nucleic acid; hybridizing the target nucleic acid and the probe nucleic acids, thereby forming hybridized products; incubating the hybridized products in an elongation solution, thereby elongating nucleotide sequence from 3'-OH end present in the hybridized region of the hybridized products; incubating the resultant products in a ligation solution to ligate the incubated probe nucleic acid to the incubated target nucleic acid; and measuring signals generated by the ligated products.

According to another embodiment, a method of determining the sequence of a target nucleic acid comprising providing a microarray comprising a substrate on which a plurality of probe nucleic acids are immobilized, wherein the sequence of the plurality of probe nucleic acids are known; providing a labeled target nucleic acid containing a sequence capable of forming a stem and loop structure at an end of the target nucleic acid; hybridizing the labeled target nucleic acid and the probe nucleic acids, thereby forming hybridized products; incubating the hybridized products in an elongation solution, thereby elongating nucleotide sequence from 3'-OH present in the hybridized region of the hybridized products; incubating the resultant products in a ligation solution to ligate the incubated probe nucleic acid to the incubated labeled target nucleic acid; and measuring signals generated by the ligated products; comparing a signal intensity from a hybridization product between a first probe nucleic acid and the labeled target nucleic acid with the intensity from a hybridization product between a second probe nucleic acid and a target nucleic acid; wherein if the signal generated from a hybridization product between a first probe nucleic acid and the labeled target nucleic acid is stronger than a signal generated by a hybridization product between a second probe nucleic acid and a target nucleic acid, it is determined that the labeled target nucleic acid contains a sequence that is perfectly complementary to the first probe nucleic acid.

BRIEF DESCRIPTION OF THE DRAWINGS

These and/or other aspects, advantages and features of the invention will become apparent and more readily appreciated from the following description of the embodiments, taken in conjunction with the accompanying drawings of which:

FIG. 1 is a diagram illustrating exemplary embodiments of hybridized nucleic acids having a detectable label (FIG. 1A), elongation (FIG. 1B) and ligation (FIG. 1C) according to an exemplary embodiment of a method of analyzing a target nucleic acid sequence.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Reference will now be made in detail to embodiments, examples of which are illustrated in the accompanying drawings.

As used herein, the term "dNTP" refers to deoxynucleoside triphosphates, the building blocks from which the DNA polymerases synthesizes a new DNA strand. dNTPs include 2'-deoxyadenosine-5'-triphosphate (dATP), 2'-deoxycytidine-5'-triphosphate (dCTP), 2'-deoxyguanosine-5'-triphosphate (dGTP), and 2'-deoxythymidine-5'-triphosphate (dTTP).

As used herein, the abbreviations "A," "T," "G," "C" and "U" describe both the ribonucleotides and the deoxyribonucleotides. The abbreviations C, A and G are used to describe both the ribonucleotides and the deoxyribonucleotides, according to context. The abbreviation T is used to describe the deoxyribonucleotide. The abbreviation U is used to describe the ribonucleotide.

In one embodiment, a method of analyzing a target nucleic acid sequence according to an embodiment of the present invention includes: providing a microarray including a substrate on which a plurality of probe nucleic acids are immobilized; providing a target nucleic acid containing a sequence capable of forming a stem and loop structure in an end of the target nucleic acid; hybridizing the target nucleic acid and the probe nucleic acids, thereby forming hybridized products; incubating the hybridized products in an elongation solution, thereby elongating nucleotide sequence from 3'-OH end present in the hybridized region of the hybridized products; incubating the resultant products in a ligation solution to ligate the incubated probe nucleic acid to the incubated target nucleic acid; and measuring signals generated by the ligated products.

The method of analyzing a target nucleic acid sequence according to the present embodiment includes providing a microarray including a substrate on which a plurality of probe nucleic acids is immobilized.

The term "microarray" is known to those of ordinary skill in the art. That is, a microarray refers to an array of probe biomolecules immobilized on a plurality of distinct regions of a substrate, wherein the probe biomolecules are for binding to a target biomolecule. Microarrays include nucleic acid microarrays, protein microarrays, antibody microarrays, and the like. A nucleic acid microarray refers to an array of probe nucleic acids immobilized on a plurality of distinct regions of a substrate, wherein the probe nucleic acids are for binding to a target nucleic acid. For a microarray, the distinct regions are also referred to as spots, and in general, at least two regions are arranged on a substrate. The probe nucleic acids may be selected from the group consisting of DNA, RNA, cDNA, mRNA, LNA, PNA and combinations thereof. The substrate may be formed of, for example, glass, silicon, plastic, ceramic, or quartz. Distinct regions refer to regions on the substrate that are distinct from each other, regardless of the shape and size thereof. The distinct regions may have a cross-sectional dimension in the range of about 10 nm to about 1000 µm, for example about 10 nm to about 10 µm. If the distinct regions have circular cross-sections, the cross-sectional dimension refers to a diameter; and if the distinct regions have non-circular cross-sections, the cross-sectional dimension refers to the length of a line passing through the center of gravity of the non-circular cross-sections. The distinct regions may be arranged with high density in the substrate. For example, about 400 or more, about $10^6$ or more, or about $10^{12}$ or more distinct regions may be arranged per square centimeter.

Each of the probe nucleic acids may be immobilized on the substrate through a 3' end or 5' end. The length of each of the probe nucleic acids may be in the range of about 15 nucleotide (nt) to about 200 nucleotides. The probe nucleic acids immobilized on the distinct region of the microarray may include different sequences or identical sequences from among each other. For example, when the probe nucleic acids are hybridized with a target nucleic acid, the probe nucleic acids immobilized on a distinct region may have five or less mismatches with the target nucleic acid. For example, when the probe nucleic acids are hybridized with a target nucleic acid, the probe nucleic acids immobilized on a distinct region may have a sequence selected from the group consisting of a perfect complementary sequence with the target nucleic acid that is perfectly hybridized, a sequence having one mismatch with the target nucleic acid, a sequence having two mismatches with the target nucleic acid, a sequence having three mismatches with the target nucleic acid, a sequence having four mismatches with the target nucleic acid, a sequence having five mismatches with the target nucleic acid, and combinations thereof. For example, the probe nucleic acids may be a probe nucleic acid for detecting SNP in a target nucleic acid, and may be selected from the group consisting of a first perfect match probe that has at a corresponding site a sequence complementary to a first allele at a SNP site within a target nucleic acid, a second perfect match probe that has at a corresponding site a sequence complementary to a second allele at the SNP site within a target nucleic acid, and a mismatch probe having a sequence that is not complementary to the first and second alleles. Herein, the first and second alleles may be the same or different from each other.

As used herein, the term "probe nucleic acid" refers to a single-stranded nucleic acid. A plurality of probe nucleic acids may be immobilized on a surface of a substrate to form a microarray and may be immobilized by in-situ synthesis or spotting. The probe nucleic acids may have a known sequence. The term "target nucleic acid" refers to a nucleic acid to be analyzed. A target nucleic acid may have a sequence complementary to a probe nucleic acid. For example, the target nucleic acid may have a sequence perfectly complementary to the probe nucleic acid or a sequence partially complementary to the probe nucleic acid that contains 1, 2, 3, 4 or 5 noncomplementary nucleotides.

Methods of manufacturing a microarray are well known in the art. For example, a microarray may be manufactured by immobilizing a probe nucleic acid that is separately synthesized to probe immobilization compounds that are immobilized on the surface of a substrate in distinct regions of the substrate. The probe immobilization compounds may include at least one compound selected from the group consisting of compounds including biotin, avidin, streptavidin, poly L-lysine, an amino group, an aldehyde group, a thiol group, a carbonyl group, a succinimide group, a maleimide group, an epoxide group, and an isothiocyanate group. Examples of the compound having an amino group include 3-aminopropyltrimethoxysilane, N-(2-aminoethyl)-3-aminopropyltrimethoxysilane (EDA), trimethoxysilylsilylpropyldiethylenetriamine (DETA), 3-(2-aminoethylaminopropyl)trimethoxysilane, and 3-aminopropyltriethoxysilane. Examples of the compound having an aldehyde group include glutaraldehyde. Examples of the compound having a thiol group include 4-mercaptopropyltrimethoxysilane (MPTS). Examples of the compound having an epoxide group include 3-glycidoxypropyltrimethoxysilane. Examples of the compound having an isothiocyanate group include 4-phenylene-diisothiocyanate (PDITC). Examples of the compound having a succinimide group and/or a maleimide group include disuccinimidyl carbonate (DSC) and succinimidyl 4-(maleimidephenyl) butylate (SMPB).

Additionally, a microarray may be manufactured by synthesizing a probe nucleic acid in distinct regions of a substrate using, for example, photolithography. When a microarray is manufactured by photolithography, a portion of a substrate coated with monomers protected with a removable group, for example a photoremovable group, is exposed to an energy source so as to remove the removable group, and then, monomers protected with the removable group are coupled and the coupling operation is repeatedly performed, thereby manufacturing an array of polynucleotides. In this regard, a polynucleotide immobilized on a polynucleotide microarray is synthesized by adding monomers one by one.

In one embodiment, a 3' end of a probe nucleic acid may be immobilized on a substrate and a 5' end may be located at a distal end of the substrate. In this case, —OH of the 5' end may be phosphorylated. The phosphoryl group may function as a substrate in a ligase-catalyzed ligation reaction. In another embodiment, the 5' end of a probe nucleic acid may be immobilized on a substrate and the 3' end may be located at a distal end of the substrate. In this case, —OH of the 3' end may function as a substrate in a polymerase-catalyzed elongation reaction. Thus, a nucleotide may be elongated from the 3'-OH.

In an exemplary embodiment, the method of analyzing a target nucleic acid sequence includes providing a target nucleic acid having a sequence capable of forming a stem and loop structure.

As used herein, the term "stem and loop structure" refers to a nucleic acid sequence that includes a double helix region (hereinafter also referred to as a "stem region") that consists of intramolecularly base paired nucleotides and a single-stranded region (hereinafter also referred to as a "loop region") interposed between double helix regions. In this specification, at least one end of 3' and 5' ends of a target nucleic acid forms the stem region and participates in intramolecular hybridization. Thus, a nucleotide of at least one end of 3' and 5' ends of a target nucleic acid is intramolecularly hybridized and includes a group selected from the group consisting of 3'-OH, 5'-OH, and 5'-H$_2$PO$_3$. A stem and loop is also known as a hairpin or hairpin loop. A stem and loop structure is formed when two regions of the same molecule, usually palindromic (reads the same in both directions, for example AAGC in one direction would read TTCG in the other and it would be a palindrome in relation to a DNA) in nucleotide sequence, base-pair to form a double helix that ends in an unpaired loop. Stability of the stem and loop structure depends on stability of the formed double helix and stability of the loop region. The stem and loop sequence itself includes a sequence that folds back on itself to form a double helix. The stability of the double helix is determined by the length of a region that is base-paired, the number of mismatches, and the base composition. In one or more embodiments, the number of mismatches may be in the range of 0 to 3, for example, 0, that is, the double helix of the stem may include a perfect complementary sequence. The loop may include, for example, at least four nucleotides, for example in the range of 4 nucleotides to about 8 nucleotides. A commonly used loop sequence may be the sequence of UUGG that is known as a tetraloop, wherein the sequence of UUGG is very stable due to a base stacking interaction of forming nucleotides. A sequence capable of forming a stem and loop structure may be CCTGCNNNNNNNGCAGG (SEQ ID No. 1), where in N is A, C, G or T; or GCCGCGGGC-CGAAAAAACCCCCCCGGCCCGCGGC (SEQ ID No. 2)

In one embodiment, the sequence capable of forming a stem and loop structure may be introduced to the target nucleic acid by ligating a sequence capable of forming a stem and loop structure to a target nucleic acid or by amplifying the target nucleic acid by using the sequence capable of forming a stem and loop structure as at least one primer. The stem and loop structure may be located at a 3' end of the target nucleic acid, a 5' end of the target nucleic acid, or the 3' and 5' ends of the target nucleic acid. Ligation of the sequence capable of forming a stem and loop structure to a target nucleic acid may be performed by using a DNA or RNA ligase. The amplification may be a polymerase chain reaction (PCR). The PCR may be performed using a nucleic acid having a sequence capable of forming a stem and loop structure as one or two primers. In addition, the sequence capable of forming a stem and loop structure may be a sequence that exists in a target nucleic acid itself.

In one embodiment, the length of the sequence capable of forming a stem and loop structure may be in the range of about 12 nucleotides to about 200 nucleotides, for example, about 15 nucleotides to about 100 nucleotides, or about 15 nucleotides to about 50 nucleotides. In the sequence capable of forming a stem and loop structure, the loop region of the loop region may be in the range of about 4 nucleotides to about 8 nucleotides, for example about 5 nucleotides to about 7 nucleotides. In the sequence capable of forming a stem and loop structure, the length of the stem region may be in the range of about 4 nucleotides to about 200 nucleotides. In the stem and loop structure, the 3' end or the 5' end is hybridized with a complementary sequence in the same molecule. If the 3' end is hybridized, in the incubating of the hybridized products, the 3' end may function as a substrate in a subsequent nucleotide elongation reaction using a polymerase. If the 5' end is hybridized, in the incubating of the hybridized products the 5' end may function as a substrate in a subsequent nucleotide elongation reaction that is catalyzed by a ligase.

In an exemplary embodiment, the target nucleic acid may be labeled with a detectable label. The detectable label may be any known detectable label. For example, the detectable label may be selected from the group consisting of a label that generates an optical signal, a radioactive label, and a label that generates an electrical signal. For example, the detectable label may be a fluorescent material that generates a fluorescent signal. Examples of the fluorescent material include fluorescein, rhodamine, Cy3 and Cy5-containing cyanines, and metal porphyrin complexes. Examples of fluorescein dye include 6-carboxylfluorescein (6-FAM) 1,2',4',1,4,-tetra chlorofluorescein (TET), 2',4',5',7',1,4-hexa chlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein, and 2'-chloro-7'-phenyl-1,4-dichloro-6-carboxyfluorescein. The fluorescein and rhodamine dyes may have a 1,4-dichloro substituent. The detectable label may be attached to an atom of a base of the target nucleic acid, for example, N-9 or C-8 position of purine or deazapurine, or a C-5 site of pyrimidine.

Methods of introducing a detectable label to a nucleic acid are well known. For example, a detectable label may be introduced to a nucleic acid by using a detectable label-containing nucleotide as a substrate in an elongation or amplification reaction of the nucleic acid. For example, when a target nucleic acid is amplified by PCR, a detectable label may be introduced to a nucleic acid by using a PCR reaction mixture that includes a detectable label-labeled dNTP as a substrate.

Methods of detecting and/or measuring a detectable label to a nucleic acid are well known. For example, for a nucleic acid labeled with label that generates an optical signal, an optical measurement device may be used. The optical measurement device may be any device that is known in the art. For example, if the nucleic acid is labeled with a fluorescent material, the optical measurement may be performed by irradiating an excitation light and measuring an emission light. The wavelengths of the excitation light and the emission light may vary according to a fluorescent material used. The excitation light may be a laser light. The emission light may be measured using an optical receiving device. The optical receiving device may be a photomultiplier tube, a photodiode, or a CCD device.

According to one embodiment, the method of analyzing a target nucleic acid sequence includes hybridizing the probe nucleic acid with the target nucleic acid. Hybridization of the probe nucleic acid with the target nucleic acid may be performed by denaturing the target nucleic acid and then incubating a solution containing the denatured target nucleic acid and the probe nucleic acid. Denaturation the target nucleic acid may be performed using heat, ultrasonic waves, chemical materials, or combinations thereof. The denaturation may be, for example, thermal denaturation. The thermal denaturation may be performed by, for example, heating the target nucleic acid to a temperature of about 70° C. to about 100° C. Also, the same denaturation process may be performed on the probe nucleic acid.

For the hybridization of the probe nucleic acid with the target nucleic acid, any incubating condition under which the denatured target nucleic acid is hybridized with the probe nucleic acid may be used without limitation. For example, the incubating temperature may be lower than a temperature at which the denaturation is performed, for example, in the range of about 0° C. to about 55° C. In addition, hybridization of the probe nucleic acid with the target nucleic acid may be performed in a solution for increasing hybridization efficiency, for example, a solution containing a material for stabilizing a double helix nucleic acid. In this regard, a hybridization buffer commonly used in the art may be used. For example, 6×SSPE (a phosphate buffered saline with EDTA solution) or 6×SSC (a citrate buffered saline solution) may be used. Buffer solutions 6×SSPE and 6×SSC are well known to one of skill and the art. Additionally, the hybridization of the probe nucleic acid with the target nucleic acid may be performed by incubating a solution including the target nucleic acid and the probe nucleic acid at a temperature of about 0° C. to about 55° C., or about 0.5° C. to about 16° C.

In one embodiment, the hybridization of the probe nucleic acid and the target nucleic acid and the formation of the stem and loop structure at an end of the target nucleic acid may be simultaneously or sequentially performed. In this specification, the meaning of "simultaneously" is not necessarily limited to the same time. For example, the term "simultaneously" includes the case that the hybridization of the probe nucleic acid and the target nucleic acid and the formation of the stem and loop structure at an end of the target nucleic acid may be performed in the same reaction, for example, in the same incubation process.

In one embodiment, the method also may include, forming a stem and loop structure at an end of the target nucleic acid before the hybridization of the probe nucleic acid with the target nucleic acid. The formation of the stem and loop structure in the target nucleic acid may be performed under appropriate hybridization conditions, as discussed in detail above. For example, the stem and loop structure may be formed by providing the target nucleic acid in a single-stranded form, denaturing the single-stranded target nucleic acid, and annealing the denatured single-stranded target nucleic acid.

In an alternative embodiment, the stem and loop structure may also be formed by denaturing the target nucleic acid and incubating a solution that contains the target nucleic acid. The denaturation may be thermal denaturation. The thermal denaturation may be performed by, for example, heating the target nucleic acid to a temperature of about 90° C. to about 100° C.

The incubating may be performed at a temperature of about 0° C. to about 55° C., for example, about 45° C. According to another embodiment, the target nucleic acid and the probe nucleic acid are denatured by heat, and then cooled to a temperature to form a stem and loop structure at an end of the target nucleic acid, and then, the temperature is further decreased to induce hybridization of the target nucleic acid and the probe nucleic acid. According to another embodiment, the target nucleic acid and the probe nucleic acid are denatured by heat, and then cooled to a temperature to induce hybridization of the target nucleic acid and the probe nucleic acid, and then, the temperature is further decreased to form a stem and loop structure at an end of the target nucleic acid.

In one embodiment, the method of analyzing a target nucleic acid sequence includes incubating the hybridized products in an elongation solution, thereby elongating nucleotide sequence from 3'-OH end present in the hybridized region of the hybridized products.

The elongation solution contains a polymerase, and catalyzes elongation of a nucleotide by using the polymerase. The elongation solution may include water, a buffer, a nucleoside triphosphate mix, and a polymerase. The water may be sterilized and purified water. For example, the water may be sterilized and distilled water. The buffer may provide a buffer condition under which the polymerase has activity to catalyze the polymerization of a nucleotide. The buffer may be appropriately selected by one of ordinary skill in the art according to the polymerase used. For example, the buffer may be a commercially available polymerase buffer corresponding to a selected polymerase. For example, the buffer may be a polymerase buffer (New England BioLabs. Inc., Cat. #B9004S) corresponding to Taq polymerase (New England BioLabs. Inc., Cat. #M0267S). The buffer selected may provide, in addition to a buffer condition under which the polymerase has activity to catalyze the polymerization of a nucleotide, and a buffer condition under which a ligase has activity to catalyze the ligation between two polynucleotides. In general, a buffer condition for a polymerase and a buffer condition for a ligase are regarded as being compatible with each other. For example, an AmpliTaq™ polymerase and an $E.\ coli$ DNA ligase may have activity in a compatible buffer condition; and a T4 DNA polymerase and a T4 DNA ligase may have activity in a compatible buffer condition. Thus, the buffer may be a polymerase buffer and/or a ligase buffer. An example of the buffer may be a buffer of AmpliTaq™ DNA polymerase Stoffel fragment, which includes nuclease-free water, 30 mM Tris-HCl (pH 8.0), 4 mM $MgCl_2$, 26 μM NAD, 1 mM DTT (Dithiothreitol), 50 μg/ml BSA, and 0.2 mM dNTP. The buffer of AmpliTaq™ DNA polymerase Stoffel fragment is available from Applied Biosystems (Cat. #N8080038). Another example of the buffer may be a buffer (1× $E.\ coli$ DNA Ligase Reaction Buffer: 30 mM Tris-HCl, 4 mM $MgCl_2$, 26 μM NAD, 1 mM Dithiothreitol, 50 μg/ml BSA, pH 8.0 at 25° C.) of $E.\ coli$ DNA ligase (New England BioLabs Cat. #M0205L). The ligase may be, for example, a T4 ligase, an $E.\ coli$ ligase, or a thermostable ligase.

The nucleoside triphosphate mix may be a dNTP or rNTP mix. The dNTP mix may be a deoxynucleoside triphosphate mix of dATP, dCTP, dGTP, dTTP or dUTP. The rNTP mix may be a ribo nucleoside triphosphate mix of rATP, rCTP, rGTP, rTTP or rUTP. The nucleoside triphosphate mix may or may not be labeled with a detectable label. The detectable label has been described above.

The polymerase may be a DNA polymerase, a RNA polymerase, or a combination thereof. For example, the polymerase may be a Taq polymerase Stoffel fragment, a reverse transcriptase, an $E.\ coli$ DNA polymerase, a Klenow fragment polymerase, a T7 RNA polymerase, a T3 RNA polymerase, a viral replicase, a SP6 RNA polymerase, or combinations thereof.

Figure 1A:
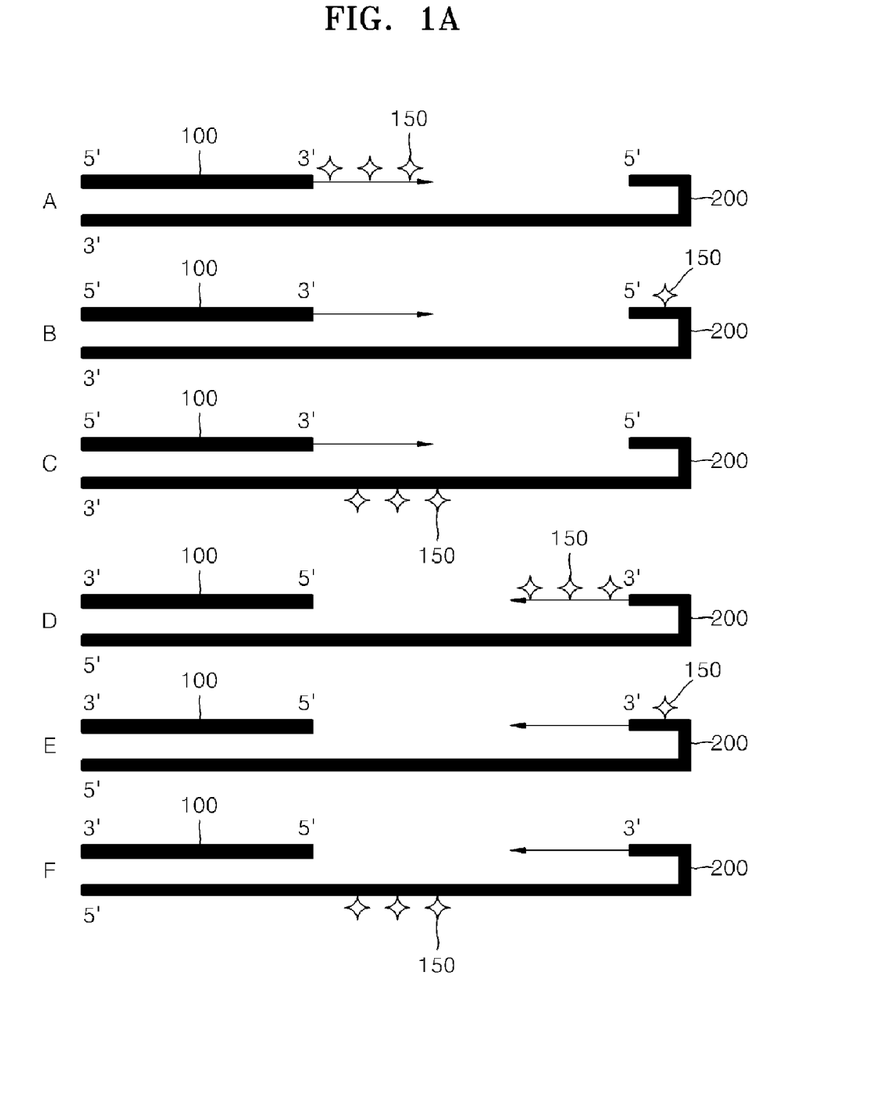

In one embodiment, when the probe nucleic acid is immobilized on a substrate through a 5' end, as demonstrated in FIG. 1A, A through C, a nucleotide may be elongated from a 3' end of the probe nucleic acid hybridized with the target nucleic acid using a nucleotide sequence of the hybridized target nucleic acid as a template. The 3' end nucleotide sequence of the probe nucleic acid may be elongated to the nucleotide just before the 5' end nucleotide in the stem and loop structure of the target nucleic acid. When a polymerase having strand displacement activity in addition to polymerase activity is used, the 3' end nucleotide sequence of the probe nucleic acid may be elongated to a nucleotide beyond the 5' end nucleotide in the stem and loop structure of the target nucleic acid by peeling off the nucleotides ahead. Elongation of the nucleic acid may not be limited to a particular mechanism.

Figure 1B:
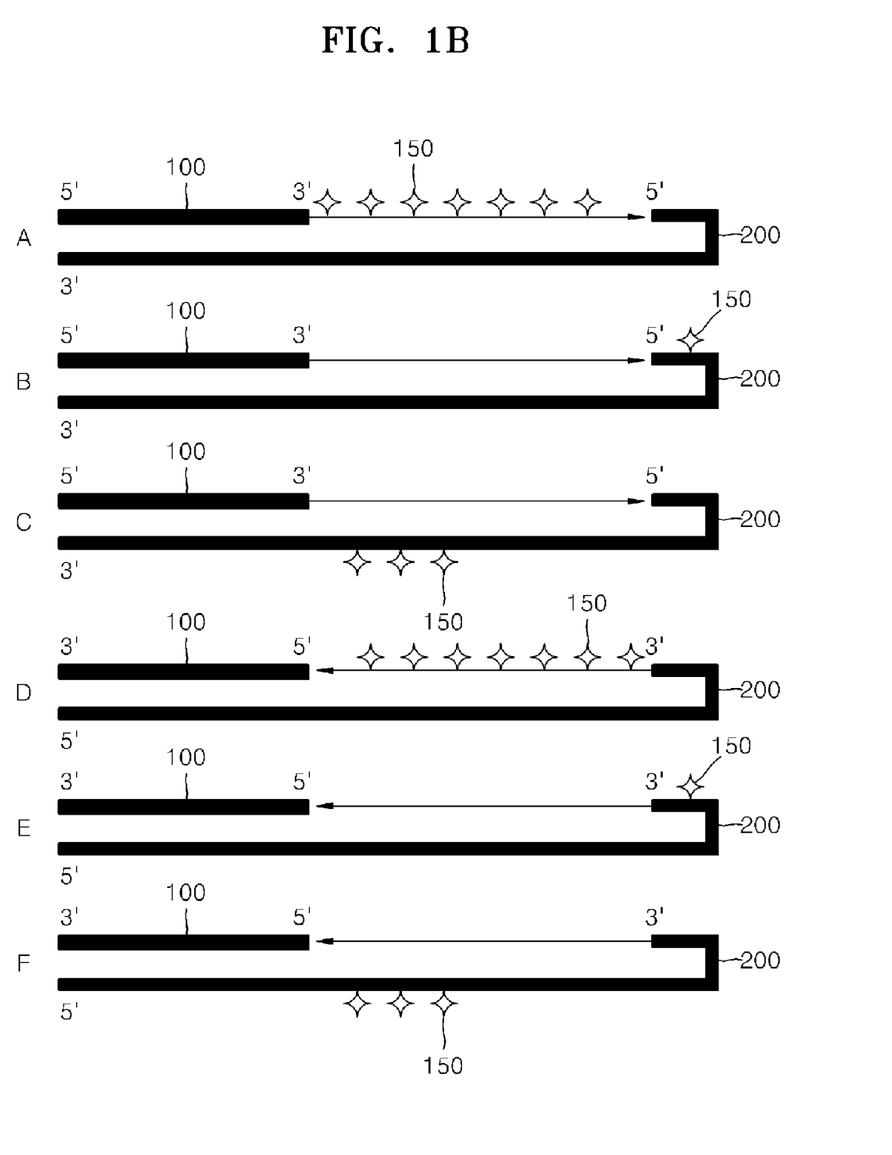

In an alternative embodiment, when the probe nucleic acid is immobilized on a substrate through the 3' end, as demonstrated in FIG. 1A, D through F, a nucleotide may be elongated from a 3' end nucleotide of a target nucleic acid intramolecularly hybridized with a complementary nucleotide in the same molecule using a nucleotide sequence of the hybridized target nucleic acid as a template, so that the nucleotide may be elongated up to a 5' end nucleotide of the probe nucleic acid, as demonstrated in FIG. 1B. However, the elongation may not be limited to a particular mechanism, and when the polymerase has a strand displacement activity, the elongation may be further performed together with the strand displacement.

In one embodiment, the method of analyzing a target nucleic acid sequence further includes incubating the resultant products in a ligation solution to ligate the incubated probe nucleic acid to the incubated target nucleic acid. Thus, the probe nucleic acid is ligated to the target nucleic acid hybridized thereto, as demonstrated in FIG. 1C.

In this regard, the ligation solution includes a ligase, and a solution for catalyzing ligation of nucleotide sequences by using the ligase. The ligation solution may include water, a buffer, and a ligase. The water may be sterilized and purified water. For example, the water may be sterilized and distilled water. The buffer may provide a buffer condition under which the ligase has activity to catalyze the ligation between two polynucleotides. The buffer may be appropriately selected by one of ordinary skill in the art according to a ligase used. For example, the buffer may be a commercially available ligase buffer corresponding to a selected ligase. For example, the buffer may be a T4 ligase buffer corresponding to T4 ligase (New England BioLabs. Inc.). The buffer may provide, in addition to a buffer condition under which the ligase has activity to catalyze the ligation between two polynucleotides, and a buffer condition under which a polymerase has activity to catalyze the polymerization of nucleotides. In general, a buffer condition for a ligase and a buffer condition for a polymerase are regarded to be compatible with each other. For example, an AmpliTaq™ polymerase and an $E.\ coli$ DNA ligase may have activity in a compatible buffer condition; and a T4 DNA polymerase and a T4 DNA ligase may have activity in a compatible buffer condition. Thus, the buffer may be a polymerase buffer and/or a ligase buffer. An example of the buffer may be a buffer of AmpliTaq™ DNA polymerase Stoffel fragment, which includes nuclease-free water, 30 mM Tris-HCl (pH 8.0), 4 mM $MgCl_2$, 26 μM NAD, 1 mM DTT (Dithiothreitol), 50 μg/ml BSA, and 0.2 mM dNTP. The buffer of AmpliTaq™ DNA polymerase Stoffel fragment may be available from Applied Biosystems (Cat. #N8080038). Another example of the buffer may be a buffer of *E. coli* DNA ligase (New England BioLabs Cat. #M0205L). The ligase may be, for example, a T4 ligase, an *E. coli* ligase, or a thermostable ligase. The ligation solution may include ATP.

For the ligation reaction, when —OH of the 5' end of the probe nucleic acid or —OH of the 5' end of the target nucleic acid is not phosphorylated, —OH of the 5' ends may be phosphorylated with a T4 polynucleotide kinase (PNK) before the hybridization. For example, —OH of the 5' ends may be phosphorylated in a solution that contains the T4 polynucleotide kinase (PNK), a PNK buffer, and rATP. If the target nucleic acid is amplified using a primer containing phoshorylated 5'-OH, the amplified target nucleic acid may have a phoshorylated 5' hydroxyl end, and thus may be directly used in the ligation reaction. If the target nucleic acid is amplified using a primer containing free 5'-OH group, the 5'-OH of the target nucleic acid may be phosphorylated with a T4 polynucleotide kinase (PNK) before hybridization.

In one embodiment, the elongation process and the ligation process may be performed in the same solution. In this regard, the same solution may include a polymerase and a ligase and provides a buffer condition under which the polymerase and the ligase have activity. Such a solution may be the same as the elongation solution or the ligation solution.

According to one embodiment, the method of analyzing a target nucleic acid sequence includes measuring a signal generated by the ligated products. The signal measurement may be performed in various manners according to the type of label in the ligated products. For example, if the ligated products are labeled with a label that generates an optical signal, an optical measurement device may be used. The optical measurement device may be any device that is known in the art. For example, if the ligated products are labeled with a fluorescent material, the optical measurement may be performed by irradiating an excitation light and measuring an emission light. The wavelengths of the excitation light and the emission light may vary according to a fluorescent material used. The excitation light may be a laser light. The emission light may be measured using an optical receiving device. The optical receiving device may be a photomultiplier tube, a photodiode, or a CCD device.

In one embodiment, the method optionally includes, after the ligation, washing the ligated products. A washing solution may be a solution suitable for removing nonligated products between a target nucleic acid and a probe nucleic acid, for example, a target nucleic acid that is not elongated, or a target nucleic acid that is elongated but is not ligated to a probe nucleic acid. The washing solution may be a buffer such as PBS. The washing condition, for example, a washing time and the number of the washing processes may be appropriately selected by one of skill in the art according to the washing solution used.

In one embodiment, the method optionally includes, after the ligation, denaturing the ligated products. Denaturation of the ligated products may be performed using heat, ultrasonic waves, chemical materials, or combinations thereof. Denaturation of the ligated products may be, for example, thermal denaturation. The thermal denaturation may be performed by, for example, heating the target nucleic acid to a temperature of about 70° C. to about 100° C. As a result of the denaturation process, a target nucleic acid that does not bind to a probe nucleic acid is removed. After the denaturation, the method may further include a washing the ligated products. The washing condition, for example, a washing time and the number of the washing processes may be appropriately selected according to the washing solution used.

In one embodiment, the method optionally includes, after the hybridization, washing the hybridized products. A washing solution may be a solution appropriate for removing an un-hybridized nucleic acid or an unreacted reactant. The washing solution may be a buffer such as SSC or PBS. The washing condition, for example, a washing time and the number of the washing processes may be appropriately selected by one of skill in the art according to the washing solution used.

The washing process of the hybridized and/or ligated products may be performed under a stringent condition. For example, the stringent condition may be such that when a probe nucleic acid is hybridized with a target nucleic acid, even a single nucleotide difference is detected. For example, the washing process may include washing with a phosphate buffered saline Tween (PBST) buffer twice for one minute, washing with a phosphate buffered saline (PBS) buffer twice for one minute, or washing with a ligase buffer once for one minute. The PBS buffer refers to a buffer that includes sodium chloride, sodium phosphate, potassium chloride and potassium phosphate, known to one of skill in the art. In this regard, the PBS buffer known in the art. The PBST buffer refers to a PBS buffer containing Tween, for example, 0.5% Tween.

In another embodiment, the method may also include determining a target nucleic acid sequence based on the measured signal.

In one embodiment, a method of determining the sequence of a target nucleic acid comprising providing a microarray comprising a substrate on which a plurality of probe nucleic acids are immobilized, wherein the sequence of the plurality of probe nucleic acids are known; providing a labeled target nucleic acid containing a sequence capable of forming a stem and loop structure at an end of the target nucleic acid; hybridizing the labeled target nucleic acid and the probe nucleic acids, thereby forming hybridized products; incubating the hybridized products in an elongation solution, thereby elongating nucleotide sequence from 3'-OH present in the hybridized region of the hybridized products; incubating the resultant products in a ligation solution to ligate the incubated probe nucleic acid to the incubated labeled target nucleic acid; and measuring signals generated by the ligated products; comparing a signal intensity from a hybridization product between a first probe nucleic acid and the labeled target nucleic acid with the intensity from a hybridization product between a second probe nucleic acid and a target nucleic acid; wherein if the signal generated from a hybridization product between a first probe nucleic acid and the labeled target nucleic acid is stronger than a signal generated by a hybridization product between a second probe nucleic acid and a target nucleic acid, it is determined that the labeled target nucleic acid contains a sequence that is perfectly complementary to the first probe nucleic acid.

The target nucleic acid sequence may be determined by comparing a signal intensity resulting from a hybridization between a first probe nucleic acid and a target nucleic acid with the signal intensity resulting from a hybridization between a second probe nucleic acid and a target nucleic acid. The first probe nucleic acid may have the same nucleotide sequence from the second probe nucleic acid except for one, two or three nucleotides. Since the sequence of probe nucleic acid is a known one, the difference in signal intensity may be used to determine the degree of hybridization between the probe nucleic acid and the target nucleic acid. A higher signal intensity indicates a higher degree of hybridization between the probe nucleic acid and the target nucleic acid, which in turn indicates an increase degree of complementarity between the between the probe nucleic acid and the target nucleic acid.

If a signal generated by a first probe region is stronger than a signal generated by a second probe region, it is determined that the target nucleic acid contains a sequence that is perfectly complementary to the first probe region. Thus, if a signal generated by a perfect match probe region is stronger than a signal generated by an imperfect match probe region, it is determined that the target nucleic acid contains a sequence that is perfectly complementary to the perfect match probe. Further, if the difference between the intensity of the signal generated by the first probe region and the intensity of the signal generated by the second probe region is insignificant, it is determined that the target nucleic acid contains a sequence that is perfectly complementary to the first probe and a sequence that is perfectly complementary to the second probe. Thus, if the difference between the intensity of the signal generated by the perfect match probe region and the intensity of the signal generated by the imperfect match probe region is insignificant, it is determined that the target nucleic acid contains a sequence that is perfectly complementary to the perfect match probe and a sequence that is perfectly complementary to the imperfect match probe.

The target nucleic acid sequence determination process may further include comparing a signal measured with a signal generated by a control target nucleic acid having a known sequence. For example, the control target nucleic acid may be a nucleic acid having completely complementary sequence with a probe or a nucleic acid having completely complementary sequence except one, two or three nucleotides with a probe.

Figure 1C:
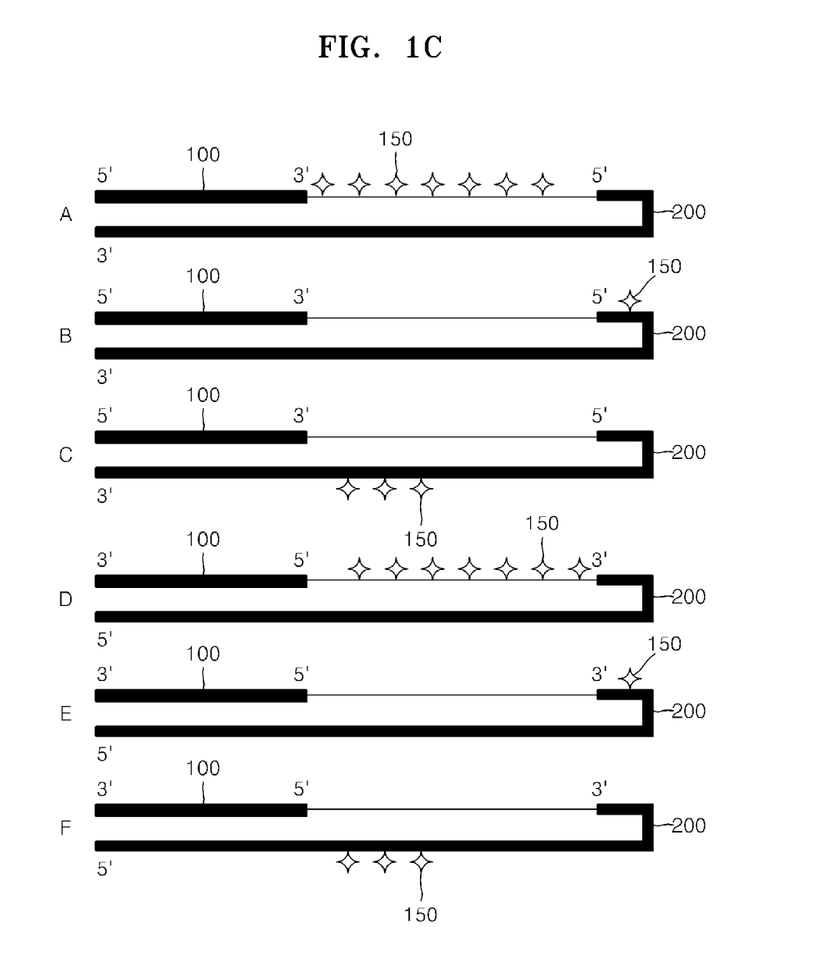

FIG. 1 is a diagram illustrating an exemplary embodiment of a method of analyzing a target nucleic acid sequence. Referring to FIG. 1A, for A through C, a probe nucleic acid 100 is immobilized on a distinct region of a substrate through a 5' end. For A through C, the probe nucleic acid 100 is hybridized with a target nucleic acid; an elongation reaction is performed elongating the probe nucleic acid from a 3' end of the probe nucleic acid using the nucleotide sequence of the hybridized target nucleic acid as a template (indicated by an arrow, see also FIG. 1B); and a ligation reaction is performed ligating the elongated probe nucleic acid with the target nucleic acid (see also FIG. 1C).

FIG. 1A, A through C, demonstrates a probe nucleic acid 100 is hybridized with a target nucleic acid 200 having a sequence capable of forming a stem and loop structure at a 5' end and the hybridization product is elongated in an elongation solution (indicated by an arrow, see also FIG. 1B). The elongation solution may include water, a buffer, a nucleoside triphosphate mix, and a polymerase. The nucleoside triphosphate mix may be a dNTP mix. The polymerase may be a Taq polymerase (New England BioLabs. Inc., Cat. #M0267S). The buffer may be a polymerase buffer (New England BioLabs. Inc., Cat. #B9004S) corresponding to a Taq polymerase. FIG. 1A, A, exemplifies an elongation reaction comprising a dNTP mix that is labeled with a label 150. For FIG. 1A, A, since the dNTP mix that is labeled with a label 150 is used, a labeled nucleotide is introduced within the elongated probe nucleic acid during the elongation reaction. For B and C, the label 150 is introduced to the target nucleic acid 200. For B, the label 150 is introduced within the sequence capable of forming a stem and loop structure of the target nucleic acid 200. For C, the label 150 is introduced within a portion of the target nucleic acid 200 other than a stem and loop structure. The resultant elongation reaction product is subjected to a ligation reaction (see also FIG. 1C). The ligation reaction may be performed using a ligation solution. The ligation solution may include water, a buffer, and a ligase. The ligase may be selected from the group consisting of T4 ligase and *E. coli* ligase, and the buffer may be selected from the group consisting of a buffer corresponding to T4 ligase and a buffer corresponding to *E. coli* ligase buffer. For A through C, the elongation of a nucleotide is initiated from 3'-OH of the probe nucleic acid 100.

FIG. 1A, D through F, demonstrates a probe nucleic acid 100 is immobilized on a distinct region of a substrate through a 3' end, and the probe nucleic acid 100 is hybridized with a target nucleic acid, and an elongation reaction and a ligation reaction are performed. For D through F, the probe nucleic acid 100 is hybridized with a target nucleic acid 200 having a sequence capable of forming a stem and loop structure at a 3' end; an elongation reaction is performed elongating the target nucleic acid from a 3' end of the target nucleic acid intramolecularly hybridized with a complementary nucleotide in the same molecule using a nucleotide sequence of the hybridized target nucleic acid as a template, so that the nucleotide may be elongated up to a 5' end nucleotide of the probe nucleic acid (indicated by an arrow, see also FIG. 1B); and a ligation reaction is performed ligating the elongated target nucleic acid with the probe nucleic acid (see also FIG. 1C). The elongation reaction is performed in an elongation solution, the elongation solution may include water, a buffer, a nucleoside triphosphate mix, and a polymerase. The nucleoside triphosphate mix may be a dNTP mix. The polymerase may be a Taq polymerase (New England BioLabs. Inc., Cat. #M0267S), and the buffer may be a polymerase buffer (New England BioLabs. Inc., Cat. #B9004S) corresponding to a Taq polymerase. FIG. 1A, D, exemplifies an elongation reaction comprising a dNTP mix that is labeled with a label 150. For FIG. 1A, D, since a dNTP mix that is labeled with a label 150 is used, a labeled nucleotide is introduced during the elongation reaction. For E and F, the label 150 is introduced to the target nucleic acid 200. For E, the label 150 is introduced to the sequence capable of forming a stem and loop structure of the target nucleic acid 200. For F, the label 150 is introduced to a portion of the target nucleic acid 200 other than a stem and loop structure. The resultant elongation reaction product is subjected to a ligation reaction. The ligation reaction may be performed using a ligation solution. The ligation solution may include water, a buffer, and a ligase. The ligase may be selected from the group consisting of a T4 ligase and an *E. coli* ligase, and the buffer may be selected from the group consisting of a buffer corresponding to a T4 ligase and a buffer corresponding to an *E. coli* ligase buffer. For D through F, the elongation of a nucleotide is initiated from 3'-OH of the target nucleic acid 200.

For A through F of FIG. 1A, an end region of the target nucleic acid 200 is hybridized with the probe nucleic acid 100. However, an inner portion of the target nucleic acid 200 may also be hybridized with the probe nucleic acid 100.

Figure 2:
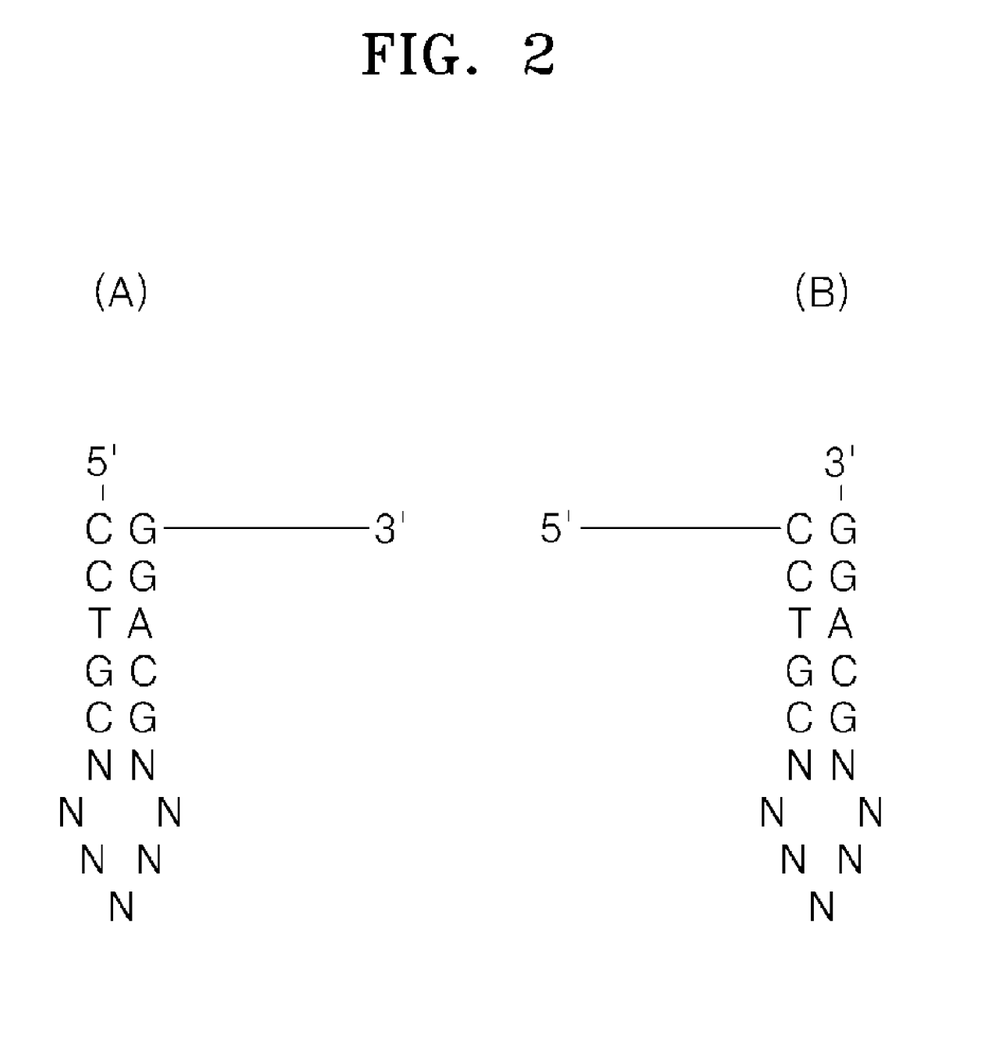
FIG. 2 is a diagram illustrating an example of a stem and loop structure that is used in one or more embodiments of the present invention. SEQ ID No. 1 (5' CCTGCNNNNNNNG-CAGG) is shown in exemplary stem and loop structures (A) and (B).

FIG. 2 is a diagram illustrating an example of a stem and loop structure that is used in one or more embodiments of the present invention. SEQ ID No. 1 (5' CCTGCNNNNNNNG-CAGG) is shown in exemplary stem and loop structures (A) and (B). In A of FIG. 2, a stem region is formed at a 5' end of a target nucleic acid, and in B of FIG. 2, a stem region is formed at a 3' end of a target nucleic acid. The —OH group of the 5' end and the —OH group of the 3' end may be free or phosphorylated. When a stem region is formed at a 5' end of a target nucleic acid, a nucleotide of the 5' end may function as a substrate in a ligase reaction; on the other hand, when a stem region is formed at a 3' end of a target nucleic acid, a nucleotide of the 3' end may function as a substrate in a polymerase reaction. In A and B of FIG. 2, a nucleotide N represents any nucleotide, including "A," "T," "G," or "C," and constitutes a loop.

Hereinafter, one or more embodiments of the present invention will be described in detail with reference to the following examples. However, these examples are not intended to limit the purpose and scope of the one or more embodiments of the present invention.

Example 1

For this example, a target nucleic acid whose sequence is to be analyzed had base sequences shown in Table 1 below. A perfect complementary probe (perfect match probe; PM probe) nucleic acid was immobilized as a probe on a substrate. The immobilized probe had a base sequence of 5'-CCAGCTATCAACTCGCGCCCTGGAA-3' (SEQ ID No. 7). The immobilized probe is perfectly complementary to a portion of the sequence designated sp1 (SEQ ID No. 3); perfectly complementary to a portion of the sequence designated sp2 (SEQ ID No. 4); and perfectly complementary to the sequence designated sp3 (SEQ ID No. 5). In this example, the target nucleic acid, sp1, was elongated and ligated by using, in addition to the sequence designated sp1 itself, a third primer sequence, that is, sp4 (SEQ ID No. 6) as a primer; the sequence designated sp2 was elongated and ligated by self-priming without the third primer; and the sequence designated sp3 represents a nucleic acid for simple hybridization.

TABLE 1

| Name | Size (nt) | Sequence | SEQ ID No. | Modification |
|---|---|---|---|---|
| sp1 | 60 | TTCCAGGGCGCGAGTTGATAGCTGGCTGG TGGCAGATGGCCCCTATAGTGAGTCGTAT TA | 3 | None |
| sp2 | 71 | TTCCAGGGCGCGAGTTGATAGCTGGCTGG TGGCAGATGGCTGCCCCTTCACAGAGAAC TTGTGAAGGGGCA | 4 | 5'-Cy3 |
| sp3 | 25 | TTCCAGGGCGCGAGTTGATAGCTGG | 5 | 5'-Cy3 |
| sp4 | 20 | TAATACGACTCACTATAGGG | 6 | 5'-Cy3 |

The sequence designated sp2 (SEQ ID No. 4) is a sequence having a stem and loop structure. The sequence designated sp3 contains a sequence that is perfectly complementary to a probe, and the sequence designated sp1 contains a sequence that is perfectly complementary to the probe and an elongated sequence, wherein the elongated sequence contains a sequence that is complementary to the sp4 sequence. The sequence designated sp4 is hybridized with the sequence designated sp1 and is then subjected to elongation and ligation reactions, thereby ligating to the sequence designated sp1.

Four types of probes were immobilized on a substrate of a microarray: a probe having a base sequence of 5'-CCAGCTATCAAATCGCGCCCTGGAA-3' (SEQ ID No. 7), a probe having a base sequence of 5'-CCAGCTATCAACTCGCGCCCTGGAA-3' (SEQ ID No. 8), a probe having a base sequence of 5'-CCAGCTATCAAGTCGCGCCCTGGAA-3' (SEQ ID No. 9), and a probe having a base sequence of 5'-CCAGCTATCAATTCGCGCCCTGGAA-3' (SEQ ID No. 10). The probes were immobilized on the surface of the substrate through 3' ends. Three microarrays were prepared. The target nucleic acids sp1, sp2 and sp3 (100 μL, 10 nM) were applied to the respective microarrays, and then incubated at a temperature of 45° C. for 1 hour, thereby hybridizing the probes with the target nucleic acids. In the experiment performed using the target nucleic acid sp-1, 5'-Cy3 labeled sp4 (the final concentration of 2 μM, Cy3-TAATACGACTCAC-TATAGGG-3': SEQ ID No. 6) that is a primer for detecting an oligonucleotide was further added to a hybridization solution and then the hybridization was performed. Then, the hybridization product was washed with a PBST buffer (137 mM NaCl, 10 mM phosphate, 0.5% Tween-20 and 2.7 mM KCl, pH 7.4) twice for one minute, a PBS buffer (137 mM NaCl, 10 mM phosphate, and 2.7 mM KCl, pH 7.4) twice for one minute, a ligase buffer (1× E. coli DNA ligase reaction buffer: 30 mM Tris-HCl, 4 mM MgCl$_2$, 26 μM NAD, 1 mM Dithiothreitol, 50 μg/ml BSA, and pH 8.0 at a temperature of 25° C.) once for one minute, thereby washing the microarrays used.

The washed microarrays were incubated in 100 μL of a polymerization and ligation solution (84 μl of nuclease-free water, 10 μl of 10× E. coli DNA ligase buffer, 2 μl of 10 mM dNTP, AmpliTaq™ DNA polymerase, 2 μl of Stoffel fragment, and 2 μl of E. coli DNA ligase) at a temperature of 37° C. for 30 minutes, so as to induce annealing, elongation and ligation reactions between the immobilized probe of each of the microarrays and a target nucleic acid in a sample.

In the microarrays used in the present experiment, four spots are defined as one spot set and the four spots consist of a spot immobilized with a probe having a nucleotide sequence of SEQ ID No. 7 on its surface through 3' end; a spot immobilized with a probe having a nucleotide sequence of SEQ ID No. 8 on its surface through 3' end; a spot immobilized with a probe having a nucleotide sequence of SEQ ID No. 9 on its surface through 3' end; and a spot immobilized with a probe having a nucleotide sequence of SEQ ID No. 10 on its surface through 3' end. The nucleotide sequences of SEQ ID Nos. 7, 8, 9 and 10 are the same except that the 12$^{th}$ nucleotides from the 5' end for SEQ ID Nos. 7, 8, 9 and 10 are A, C, T, G and T, respectively. 100 numbers of the spot set are arrayed at different sites in each of the microarrays. Thus, each microarray contained 100 numbers of the spot set. Further, a base of the 12$^{th}$ nucleotide from the 5' end is determined by comparing signals emitted from A, C, G and T spots belonging to one SNP site through a statistical process performed using a median value and standard deviation of fluorescent signals emitted from 100 identical probes, respectively. Experimental values obtained using the three microarrays were compared. As a result, it was identified that when a target nucleic acid containing a stem and loop structure was used, better results were obtained compared to the other methods. That is, when the target nucleic acid sp2 containing the stem and loop structure was used, a target nucleic acid sequence was efficiently identified.

As described above, according to a method of analyzing a target nucleic acid sequence according to the one or more of the above embodiments of the present invention, the target nucleic acid sequence can be identified with high sensitivity and high accuracy.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of analyzing a target nucleic acid sequence, the method comprising:
   providing a microarray comprising a substrate on which a plurality of probe nucleic acids are immobilized;
   providing a target nucleic acid containing a sequence capable of forming a stem and loop structure at an end of the target nucleic acid;
   hybridizing the target nucleic acid and the probe nucleic acids, thereby forming hybridized products;
   elongating a nucleotide sequence from a 3'-OH present in the hybridized region of the hybridized products in an elongation solution;
   incubating the resultant products in a ligation solution to ligate the incubated probe nucleic acid to the incubated target nucleic acid; and
   measuring signals generated by the ligated products.

2. The method of claim 1, wherein the sequence capable of forming a stem and loop structure is introduced to the target nucleic acid by ligation to the target nucleic acid.

3. The method of claim 1, wherein the sequence capable of forming a stem and loop structure is introduced to the target nucleic acid by amplifying the target nucleic acid by using the sequence capable of forming a stem and loop structure as a primer.

4. The method of claim 1, wherein the length of the sequence capable of forming a stem and loop structure is in the range of 12 nucleotides to 200 nucleotides.

5. The method of claim 1, wherein the length of a loop region of the sequence capable of forming a stem and loop structure is in the range of 4 nucleotides to 8 nucleotides.

6. The method of claim 1, wherein the length of a stem region of the sequence capable of forming a stem and loop structure is in the range of 4 nucleotides to 200 nucleotides.

7. The method of claim 1, wherein the target nucleic acid is labeled with a detectable label.

8. The method of claim 7, wherein the detectable label is selected from the group consisting of a label that generates an optical signal, a radioactive label, and a label that generates an electrical signal.

9. The method of claim 1, wherein the hybridization is performed by denaturing the target nucleic acid and then incubating a solution comprising the denatured target nucleic acid and the probe nucleic acids.

10. The method of claim 9, wherein the denaturation comprises thermal denaturation.

11. The method of claim 1, wherein hybridization of the probe nucleic acid and the target nucleic acid and formation of the stem and loop structure in an end of the target nucleic acid occur simultaneously.

12. The method of claim 1, before the hybridization, further comprising forming the stem and loop structure in an end of the target nucleic acid.

13. The method of claim 12, wherein the stem and loop structure is formed by denaturing the target nucleic acid and incubating the denatured target nucleic acid.

14. The method of claim 13, wherein the denaturation comprises thermal denaturation.

15. The method of claim 1, wherein the elongation solution comprises water, a buffer, a nucleoside triphosphate mix, and a polymerase.

16. The method of claim 15, wherein the nucleoside triphosphate mix comprises a dNTP or rNTP mix.

17. The method of claim 15, wherein the nucleoside triphosphate mix is labeled with a detectable label.

18. The method of claim 15, wherein the buffer comprises a polymerase buffer or a ligase buffer.

19. The method of claim 1, wherein the ligation solution comprises water, a buffer, and a ligase.

20. The method of claim 19, wherein the buffer comprises a polymerase buffer or a ligase buffer.

21. The method of claim 1, wherein the incubating of the hybridized products and the incubating of the resultant products are performed in the same solution.

22. The method of claim 1, after the incubating of the resultant products, further comprising washing the incubated products.

23. The method of claim 1, after the incubating of the resultant products, further comprising denaturing the incubated products.

24. The method of claim 1, after the hybridization, further comprising washing the hybridized products.

25. The method of claim 1, further comprising determining the target nucleic acid sequence based on the signal measured.

26. The method of claim 25, wherein, if a signal generated by a first probe region is stronger than a signal generated by an second probe region, it is determined that the target nucleic acid contains a sequence that is perfectly complementary to the first probe region.

27. The method of claim 24, wherein, if the difference between the intensity of the signal generated by the first probe region and the intensity of the signal generated by the second probe region is insignificant, it is determined that the target nucleic acid contains a sequence that is perfectly complementary to the first probe and a sequence that is perfectly complementary to the second probe.

28. The method of claim 25, further comprising comparing the signal measured with a signal obtained from a control target nucleic acid having a known sequence.

29. A method of determining the sequence of a target nucleic acid comprising
   providing a microarray comprising a substrate on which a plurality of probe nucleic acids are immobilized, wherein the sequence of the plurality of probe nucleic acids are known;
   providing a labeled target nucleic acid containing a sequence capable of forming a stem and loop structure at an end of the target nucleic acid;
   hybridizing the labeled target nucleic acid and the probe nucleic acids, thereby forming hybridized products;
   incubating the hybridized products in an elongation solution, thereby elongating nucleotide sequence from a 3'-OH present in the hybridized region of the hybridized products;
   incubating the resultant products in a ligation solution to ligate the incubated probe nucleic acid to the incubated labeled target nucleic acid; and
   measuring signals generated by the ligated products;
   comparing a signal intensity from a hybridization product between a first probe nucleic acid and the labeled target nucleic acid with the intensity from a hybridization product between a second probe nucleic acid and a target nucleic acid; wherein if the signal generated from a hybridization product between a first probe nucleic acid and the labeled target nucleic acid is stronger than a signal generated by a hybridization product between a second probe nucleic acid and a target nucleic acid, it is determined that the labeled target nucleic acid contains a sequence that is perfectly complementary to the first probe nucleic acid.

* * * * *

SEQUENCE LISTING

```
<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: stem and loop sequence
<220> FEATURE:
<221> NAME/KEY: variation
<222> LOCATION: (6)
<223> OTHER INFORMATION: n=A, C, G or T
<220> FEATURE:
<221> NAME/KEY: variation
<222> LOCATION: (7)
<223> OTHER INFORMATION: n=A, C, G or T
<220> FEATURE:
<221> NAME/KEY: variation
<222> LOCATION: (8)
<223> OTHER INFORMATION: n=A, C, G or T
<220> FEATURE:
<221> NAME/KEY: variation
<222> LOCATION: (9)
<223> OTHER INFORMATION: n=A, C, G or T
<220> FEATURE:
<221> NAME/KEY: variation
<222> LOCATION: (10)
<223> OTHER INFORMATION: n=A, C, G or T
<220> FEATURE:
<221> NAME/KEY: variation
<222> LOCATION: (11)
<223> OTHER INFORMATION: n=A, C, G or T
<220> FEATURE:
<221> NAME/KEY: variation
<222> LOCATION: (12)
<223> OTHER INFORMATION: n=A, C, G or T

<400> SEQUENCE: 1
cctgcnnnnn nngcagg                                                17

<210> SEQ ID NO 2
<211> LENGTH: 34
<212> TYPE: DNA
<213> ORGANISM: Artificial Sequence
<220> FEATURE:
<223> OTHER INFORMATION: stem and loop sequence

<400> SEQUENCE: 2
gccgcgggcc gaaaaaaccc ccccggcccg cggc                              34

<210> SEQ ID NO 3
<211> LENGTH: 60
<212> TYPE: DNA
<213> ORGANISM: Artificial Sequence
<220> FEATURE:
<223> OTHER INFORMATION: sp1: target sequence

<400> SEQUENCE: 3
ttccagggcg cgagttgata gctggctggt ggcagatggc ccctatagtg agtcgtatta   60

<210> SEQ ID NO 4
<211> LENGTH: 71
<212> TYPE: DNA
<213> ORGANISM: Artificial Sequence
<220> FEATURE:
<223> OTHER INFORMATION: sp2: 5'-Cy3 labelled

<400> SEQUENCE: 4
ttccagggcg cgagttgata gctggctggt ggcagatggc tgccccttca cagagaactt   60
```

-continued gtgaaggggc a                                                          71

<210> SEQ ID NO 5
<211> LENGTH: 25
<212> TYPE: DNA
<213> ORGANISM: Artificial Sequence
<220> FEATURE:
<223> OTHER INFORMATION: sp3: 5'-Cy3 labelled

<400> SEQUENCE: 5
ttccagggcg cgagttgata gctgg                                           25

<210> SEQ ID NO 6
<211> LENGTH: 20
<212> TYPE: DNA
<213> ORGANISM: Artificial Sequence
<220> FEATURE:
<223> OTHER INFORMATION: sp4: 5'-Cy3 labelled

<400> SEQUENCE: 6
taatacgact cactataggg                                                 20

<210> SEQ ID NO 7
<211> LENGTH: 25
<212> TYPE: DNA
<213> ORGANISM: Artificial Sequence
<220> FEATURE:
<223> OTHER INFORMATION: Probe

<400> SEQUENCE: 7
ccagctatca aatcgcgccc tggaa                                           25

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
ccagctatca actcgcgccc tggaa                                           25

<210> SEQ ID NO 9
<211> LENGTH: 25
<212> TYPE: DNA
<213> ORGANISM: Artificial Sequence
<220> FEATURE:
<223> OTHER INFORMATION: Probe

<400> SEQUENCE: 9
ccagctatca agtcgcgccc tggaa                                           25

<210> SEQ ID NO 10
<211> LENGTH: 25
<212> TYPE: DNA
<213> ORGANISM: Artificial Sequence
<220> FEATURE:
<223> OTHER INFORMATION: Probe

<400> SEQUENCE: 10
ccagctatca attcgcgccc tggaa                                           25